United States Patent
Handler

(10) Patent No.: US 8,398,844 B2
(45) Date of Patent: Mar. 19, 2013

(54) METHOD FOR DIAGNOSING A NOX READINGS RECORDER

(75) Inventor: Torsten Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 328 days.

(21) Appl. No.: 12/915,701

(22) Filed: Oct. 29, 2010

(65) Prior Publication Data

US 2011/0100842 A1    May 5, 2011

(30) Foreign Application Priority Data

Oct. 30, 2009   (DE) .......................... 10 2009 046 232

(51) Int. Cl.
    *G01N 27/419* (2006.01)
(52) U.S. Cl. .................... 205/784.5; 205/781; 204/411; 204/424; 204/426; 73/23.31; 123/703
(58) Field of Classification Search .......... 204/400–402, 204/404, 406–412, 415–435; 205/775.5, 205/780.5–781, 782.5–785.5, 787; 73/23.31, 73/23.32; 123/672–704
    See application file for complete search history.

(56) References Cited

U.S. PATENT DOCUMENTS

| | | | |
|---|---|---|---|
| 5,877,413 A * | 3/1999 | Hamburg et al. ........ | 73/114.75 |
| 6,290,829 B1 | 9/2001 | Kato et al. | |
| 6,471,840 B1 | 10/2002 | Gao et al. | |
| 7,427,347 B2 | 9/2008 | Bausewein et al. | |
| 2001/0052473 A1 | 12/2001 | Ohkuma | |
| 2008/0296174 A1 * | 12/2008 | Ding et al. .................... | 205/781 |

FOREIGN PATENT DOCUMENTS

| | | |
|---|---|---|
| DE | 103 12 732 | 12/2005 |
| DE | 10 2006 053 841 | 5/2008 |
| WO | WO 2008/058832 | 5/2008 |

* cited by examiner

*Primary Examiner* — Keith Hendricks
*Assistant Examiner* — Susan D Leong
(74) *Attorney, Agent, or Firm* — Merchant & Gould P.C.

(57) ABSTRACT

Method for diagnosing a NOx readings recorder which acquires a NOx concentration in an exhaust gas tract of an internal combustion engine and comprises two measuring chambers (110, 120), wherein the exhaust gas to be measured is supplied to the first measuring chamber (110) and an oxygen concentration is set by means of a first oxygen ion pump current ($I_{P1}$), wherein the second measuring chamber (120) is connected to said first measuring chamber (110) and wherein both measuring chambers are disposed in a solid electrolyte, the oxygen content in the second measuring chamber (120) is determined; the oxygen content is additionally determined by a separate device; the two values characterizing the oxygen concentration are compared and a defective sensor is then suggested if the oxygen concentration value determined in the second measuring chamber (120) deviates from the oxygen concentration value determined by the separate sensor device by a predeterminable magnitude.

5 Claims, 2 Drawing Sheets

METHOD FOR DIAGNOSING A NOX READINGS RECORDER

This application claims benefit of Serial No. 10 2009 046 232.5, filed 30 Oct. 2009 in Germany and which application is incorporated herein by reference. To the extent appropriate, a claim of priority is made to the above disclosed application.

BACKGROUND

The invention relates to a method for diagnosing a NOx readings recorder which acquires a NOx concentration in an exhaust gas tract of an internal combustion engine and comprises two measuring cells, wherein the exhaust gas to be measured is supplied to the first measuring cell and an oxygen concentration is set by means of a first oxygen ion pump current, wherein the second measuring cell is connected to said first measuring cell and wherein both measuring cells are disposed in a solid electrolyte.

The invention also further relates to a computer program and a computer program product, which are suitable for carrying out the method.

In order to reduce the fuel consumption of motor vehicles, internal combustion engines are increasingly being operated with a lean fuel/air mixture. The efficiency of the internal combustion engine is particularly high in this so-called lean operation. In order to meet the stringent exhaust emission limits, a particular exhaust gas aftertreatment is then required, which especially allows for a reduction of nitrogen oxides (NOx) in the exhaust gas.

For this reason, so-called NOx storage catalytic converters are used, which are capable of adsorbing NOx compounds that arise during lean combustion out of the exhaust gas. An "evacuation" of such a NOx catalytic converter is necessary from time to time. Evacuation thereby means as much as conversion of NOx compounds to harmless compounds. In so doing, carbon monoxide, hydrogen and hydrocarbon are, for example, worth considering as reducing agents. A NOx sensor, respectively NOx readings recorder, is disposed downstream of the NOx storage catalytic converter in the exhaust gas duct for the determination of the degree of loading of said NOx storage catalytic converter and for the initiation of the regeneration of said NOx storage catalytic converter.

As an alternative to the exhaust gas aftertreatment by means of NOx storage catalytic converters, so-called selective catalytic reaction systems can be used. A NOx readings recorder is likewise used for the control of said systems.

A NOx readings recorder of this kind is known, for example, from the American patent publication U.S. Pat. No. 6,290,829 B1.

A NOx readings recorder of this kind constitutes an exhaust emission-relevant part. Exhaust emission-relevant parts must be continually and constantly checked for their operability. Such checks are required by law in both Europe and America. In the future, monitoring limit values will have to be complied with for monitoring NOx emissions.

In order to meet this objective, it is necessary within the scope of the on-board diagnostics (OBD) to monitor all components which serve to reduce nitrogen oxides in motor vehicles for the operability thereof. Hence a faulty NOx readings recorder from model year 2009 will, for example, have to be detected as faulty when a value 3.5 times that of the limit value is exceeded, from model year 2010 when a value 2.5 times that of the limit value is exceeded and from model year 2013 when a value 1.5 times that of the limit value is exceeded.

Only serious errors of the NOx sensor can be recognized using current diagnostics known per se.

Moreover, a monitoring of a characteristic curve drift in vehicles with diesel internal combustion engines has not been possible up until now because on the one hand no NOx emissions are present in the test cycle after a selective catalytic reduction (SCR—selective catalytic reduction—Nox reduction catalytic converter with urea injection). On the other hand, it is virtually impossible in diesel systems of this type to set exact and known NOx concentrations by means of engine-related measures. In such a system, a reference NOx value cannot be set and is not available.

A plausibility check of the communication of the NOx sensors between themselves is likewise not possible because this would entail an active conversion reduction for a long period of time, which would result in the SCR storage system having to be run empty. This in turn would lead to the NOx emissions being significantly increased at times during the test cycle and driving operation.

In the case that NOx sensors are present, so-called internal "self-diagnoses" are known from the technical field for gasoline operated engines under stoichiometric conditions ($\delta=1$). These self-diagnoses are, for example, described in the German patent publication DE 103 12 732 B4 as well as in the German patent publication DE 10 2006 053 841A1. An application at $\delta=1$ is, however, extremely difficult to carry out in diesel systems. In other words, conditions for stability (e.g. a stable $\delta$) required for a successful self-diagnosis are not feasible. Additional disadvantages of an internal self-diagnosis of this type are:

- complex interventions into the pump current regulator of the NOx sensor are required;
- very stable exhaust gas conditions are required, which often are not feasible when the vehicle is in operation;
- as a result of a targeted setting of an $O_2$ partial pressure in the second chamber of the NOx readings recorder and comparison with a reference value, effects of drift and ageing on the pump electrodes can distort the outcome.

The aim of the invention is therefore to convey a method for diagnosing a NOx readings recorder, particularly for recognizing the presence of a characteristic curve drift of such a NOx sensor, in diesel vehicles which delivers a diagnostic result at various operating points during driving operation as well as within restricted test cycles; thus enabling statutory exhaust emission limits to be met.

SUMMARY

This aim is met by a method for diagnosing a NOx sensor of the kind described at the beginning of the application using the following steps:

- the pump voltage at an inner pump electrode in the first measuring chamber and at an oxygen measuring electrode in the second measuring chamber is reduced at a predetermined, respectively predeterminable, operating point such that the oxygen content of the exhaust gas appears in the second measuring chamber at a NOx electrode disposed therein;
- said oxygen content in the second measuring chamber is determined by means of the NOx measuring electrode;
- said oxygen content is additionally determined by means of a separate device;
- the two values characterizing the oxygen concentration are compared and a defective sensor is then suggested if the oxygen concentration value determined in the second chamber with the aid of the pump current deviates from the oxygen concentration value determined by means of the separate sensor device by a predeterminable magnitude.

It is the basic idea of the invention to assess the operability of the NOx sensor by means of a comparison between the oxygen concentration, respectively oxygen content, acquired using said sensor and an oxygen value acquired using a separate device.

If the oxygen concentration acquired by means of the NOx readings recorder deviates from that oxygen concentration, which was determined with the separate device, by a predeterminable magnitude or tolerance threshold, a defective NOx sensor is suggested. The advantage of this method is that it can be carried out at various operating points during the normal operation of the internal combustion engine. Said method can also be carried out within restricted test cycles in order to deliver a monitoring result, which allows for conclusions to be drawn about the operability of the NOx sensor and thereby conclusions about the compliance with predetermined tight exhaust gas limit values of the internal combustion engine.

Advantageous modifications and improvements to the method stated in the independent claims are possible by means of the measures listed in the dependent claims. Provision can, for example, be made for the separately acquired oxygen content to be detected by a separate sensor device, for example by a 8-sensor and/or a second NOx sensor.

Basically speaking, the separate oxygen content can also, however, be determined with mathematical methods using data which is present and which characterizes the operating point of the internal combustion engine.

The predeterminable operating point, during which the method for diagnosing the NOx sensor is carried out, is preferably characterized by a steady-state oxygen concentration content.

The invention particularly provides that the oxygen content in the exhaust gas is reduced to a predeterminable value, in particular to a value <3% oxygen content, during the diagnosis.

The predeterminable operating point is furthermore thereby characterized in that the NOx content with respect to the oxygen content to be measured is negligibly small, namely in particular <than 100 ppm at <3% oxygen content.

BRIEF DESCRIPTION OF THE DRAWINGS

Further advantages and features of the invention are the subject matter of the following description and the graphic depiction of exemplary embodiments of the invention. Features can thereby in each case be implemented individually or also in combination with each other.

The following are shown.

DETAILED DESCRIPTION

Figure 1:
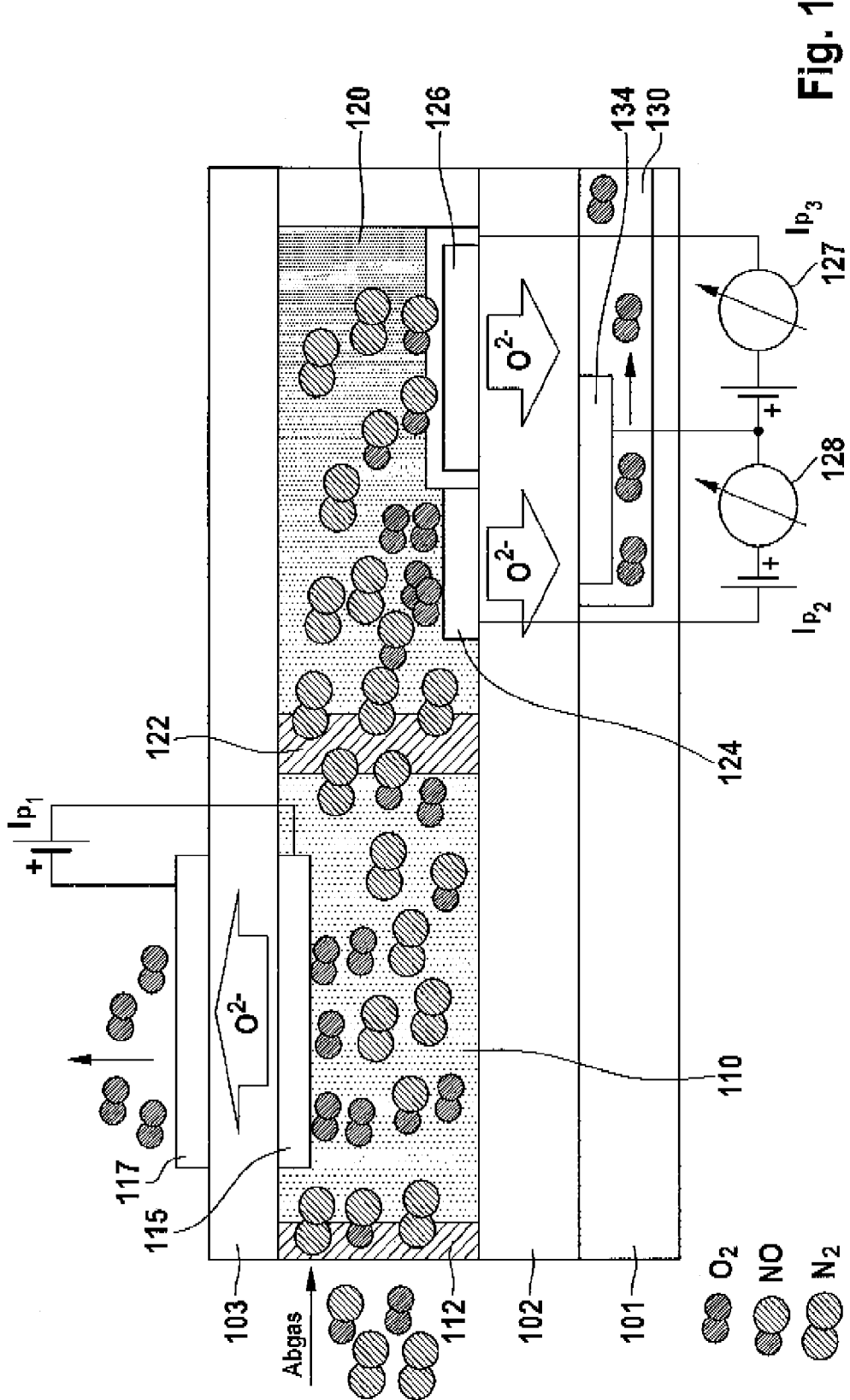
FIG. 1 is schematically a NOx readings recorder in the case of which the method according to the invention is used and FIG. 2 a flow diagram of the method according to the invention.

A NOx gas sensor, which is used to detect gases present in exhaust gases, such as NO, $NO_2$ and $O_2$, is schematically depicted in FIG. 1. A gas sensor of this type consists of laminated electrolyte layers 101, 102, 103. The electrolyte can, for example, be zirconium oxide. Two chambers are configured in the sensor, a first chamber 110 and a second chamber 120. The first chamber 110 is separated from the exhaust gas by a porous diffusion layer 112. The second chamber 120 is separated from said first chamber 110 by a porous diffusion layer 122. An inner pump electrode 115 is disposed in the first chamber, and an outer pump electrode 117 is disposed opposite thereto and so as to be exposed to the exhaust gas. A pump voltage is applied to the inner and the outer pump electrode as depicted in FIG. 1. Said first chamber 110 serves to remove the oxygen $O_2$ from the said first chamber 110. The pump current $I_{P1}$ is proportional to the oxygen $O_2$ and is thereby a measurement for the proportion of oxygen in the exhaust gas. The measuring gas can have constituents from NOx, for example NO, $N_2$ and $O_2$. A so-called $O_2$ electrode 124 as well as NOx measuring electrode 126 disposed beneath a porous diffusion layer is provided in the second chamber 120. An air reference electrode 134 is disposed in an air reference space 130, which is positioned beneath said second chamber 120. Basically speaking, the electrode 124 can be connected to the inner pump electrode 115 via a voltage source (Such a connection is not depicted). By means of an arrangement of this kind, it is possible for the oxygen partial pressure to be precisely set in the measuring gas. In the circuit depicted in FIG. 1, the electrode 124 is connected to the air reference electrode 134 via a voltage source. The measuring current $I_{P2}$ is acquired by an ammeter 128. In contrast, an electrochemical reduction of nitrogen oxides NOx, for example NO to $N_2$ and $O_2$, takes place at the actual NOx measuring electrode 126, in this case a transport of oxygen ions taking place from the NOx measuring electrode 126 into the air reference space 130, as is indicated by an arrow $O^{2-}$. The NOx measuring electrode 126 is connected to the air reference electrode 134 likewise via a voltage source, and the NOx measuring current $I_{P3}$ is acquired by an ammeter 127, as is schematically depicted in FIG. 1. The determination of the NO concentration in the exhaust gas is possible by means of this arrangement. If the proportion of oxygen is namely very small at the NOx, respectively NO, electrode, the pump current $I_{P3}$ is proportional to the concentration of nitrogen oxide because oxygen can only develop from nitrogen oxide.

A basic idea of the method according to the invention is then to compare the oxygen concentration acquired by the NOx sensor depicted in FIG. 1 with an oxygen concentration in the exhaust gas additionally acquired, for example, by an external 8-sensor; and in the event that the two signals deviate from one another by a predetermined limit value, a defective NOx sensor is suggested. Said method is based on the fact that the oxygen concentration instead of the NOx concentration is measured at the NOx electrode 126. For this reason, the pump voltage at the two oxygen electrodes, the inner pump electrode 115 and the measuring electrode 124, is reduced at a suitable operating point, which is characterized by a constant $O_2$ content such that a transport of oxygen toward the NOx measuring electrode 126 takes place. The oxygen is transformed at the NOx measuring electrode 126 and the current $I_{P3}$ measured, for example, using the ammeter 127 is a measurement for the oxygen concentration in the exhaust gas. In so doing, a separate control and tracking of the pump voltage is required. Moreover, it may be necessary to calibrate the oxygen characteristic curve of the NOx measuring electrode 126. This is done prior to the onset of said method. When using the NOx sensor later on for the described purpose, such a calibration is no longer required. Furthermore, said method takes place at an oxygen content in the exhaust gas, which is reduced to <3% oxygen. This reduction can, for example, be set by means of a 8-control. In addition, a further requirement for carrying out said method, particularly for increasing the accuracy of the acquisition of the oxygen concentration, is that the NOx concentration is negligibly small with respect to the oxygen concentration to be measured and particularly that <100 ppm NOx are present at <3% oxygen.

Figure 2:
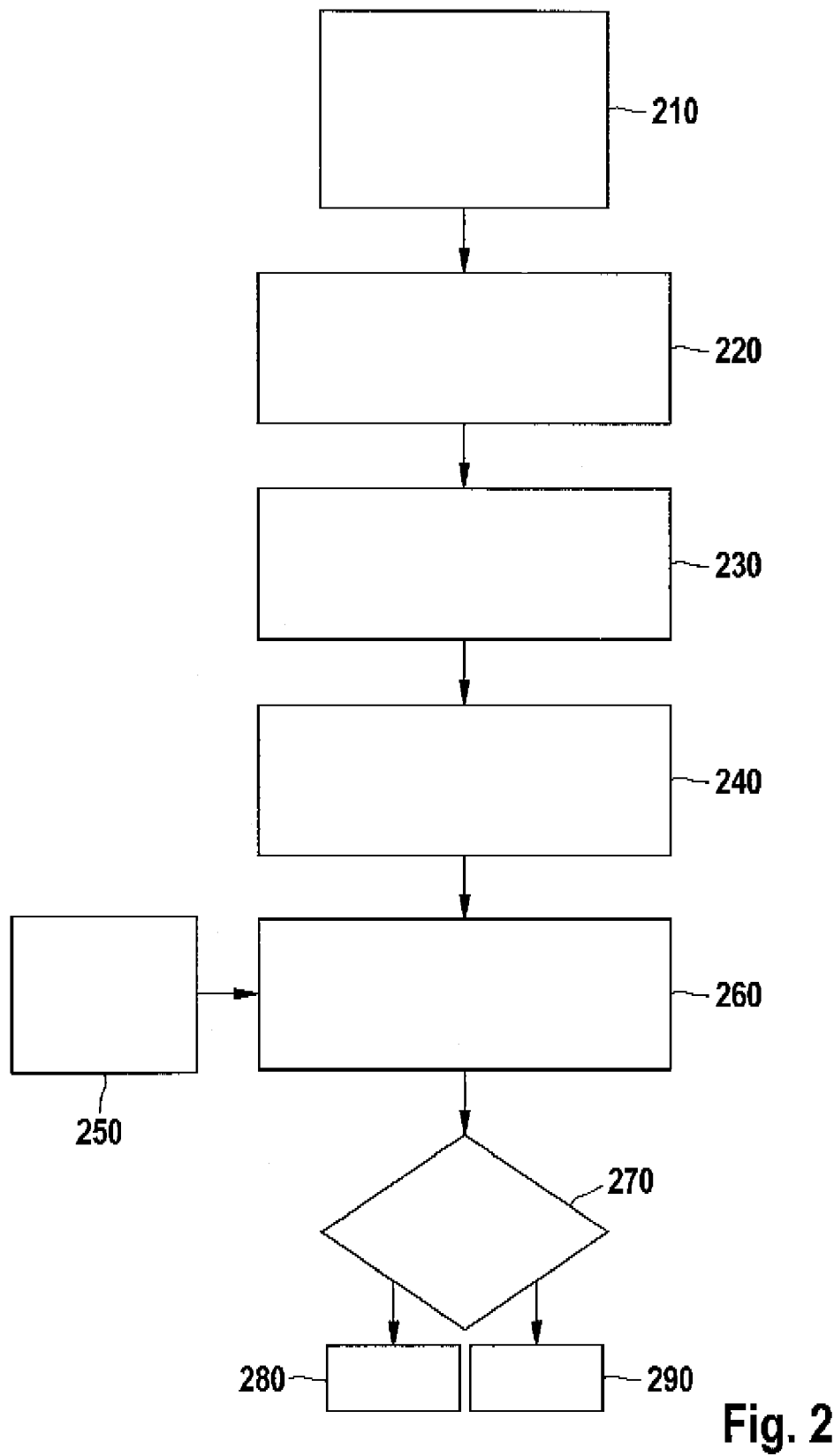

In connection with FIG. 2, the sequence of the course of events of the method is explained using a flow diagram. In step 210, the selection of the operating conditions takes place, in particular the setting of a constant lambda. For this purpose, systems such as the exhaust gas recirculation, the injection timing, the throttle valve adjustment and the like are changed. The diagnosis begins in step 220. The pump voltages at the inner pump electrode as well at the electrode 124 are reduced. A pause is made in step 230 until a stable oxygen content is present in the second chamber 120 and thereby at the NOx electrode. The oxygen content is determined using a separate characteristic curve, which was determined in advance (step 240). Simultaneously to this event in step 240, the oxygen content is determined in step 250 by means of a wideband lambda probe or with the aid of a second NOx sensor or the like. In step 260, the values ascertained in this manner for said oxygen content are related to one another, for example subtracted from each other and are compared with each other in step 270, for example the difference is compared with predeterminable values (error bound). If the oxygen content determined by means of the external sensor device is greater than the oxygen content as it was ascertained by the NOx measuring probe 126 in the manner described above, and if the difference exceeds the predeterminable error bound, the probe is recognized as being defective in step 280. If on the other hand the oxygen value is within the predeterminable error bound, the NOx sensor is recognized to be functioning properly.

The advantage of the method previously described is that it is possible to monitor the NOx readings recorder at various operating points during the operation of the internal combustion engine as well as during restricted test cycles and to make assessments about the operability thereof.

The method previously described can, for example, be implemented as a computer program on a computer, in particular in a control unit (known per se) of an internal combustion engine and run thereon, respectively therein. The program code can be stored on a machine-readable carrier, which the control unit can read. In this manner, the method can be upgraded in vehicles equipped with NOx readings recorders of the type described above. Because 8-probes already present per se in internal combustion engines can be used to separately acquire the oxygen content, no additional hardware expense is required in this respect.

The invention claimed is:

1. Method for diagnosing a NOx readings recorder which acquires a NOx concentration in an exhaust gas tract of an internal combustion engine and comprises two measuring chambers, wherein the exhaust gas to be measured is supplied to the first measuring chamber and an oxygen concentration is set by means of a first oxygen ion pump current, wherein the second measuring chamber is connected to said first measuring chamber and wherein both measuring chambers are disposed in a solid electrolyte, comprising the following steps:

the pump voltage at an inner pump electrode in said first measuring chamber and at an oxygen electrode in said second measuring chamber is reduced at a predeterminable operating point such that the oxygen concentration of the exhaust gas appears in the second measuring chamber at a NOx measuring electrode disposed therein;

the oxygen concentration in said second measuring chamber (120) is determined by means of the NOx measuring electrode (126);

said oxygen concentration is additionally determined by means of a separate device; the two oxygen concentration values are compared and a defective sensor is then suggested if the oxygen concentration value determined in the second measuring chamber deviates from the oxygen concentration value determined by means of the separate sensor device by a predeterminable magnitude.

2. The method according to claim 1, wherein the device for separately determining the oxygen concentration is a computing device for the computational determination of the oxygen concentration.

3. The method according to claim 1, wherein the predeterminable operating point is a steady-state oxygen concentration.

4. The method according to claim 1, wherein the oxygen concentration in the exhaust gas is reduced to a predeterminable value of <3% oxygen concentration.

5. The method according to claim 1, wherein the predeterminable operating point is when the NOx content is smaller than 100 ppm NOx at 3% oxygen concentration.

\* \* \* \* \*